United States Patent [19]
Schwartz et al.

[11] Patent Number: 5,877,220
[45] Date of Patent: Mar. 2, 1999

[54] AMIDE-BASED OLIGOMERIC CATIONIC LIPIDS

[75] Inventors: David Aaron Schwartz, Encinitas; Brian Patrick Dwyer, San Diego; William J. Daily, Atascadero; Kumar Srinivasan, San Diego; Bob Dale Brown, Encinitas, all of Calif.

[73] Assignee: Genta, Incorporated, San Diego, Calif.

[21] Appl. No.: 812,775

[22] Filed: Mar. 6, 1997

[51] Int. Cl.⁶ .......................... A01N 37/18; A01N 47/10; C07C 233/05
[52] U.S. Cl. .......................... 514/626; 514/613; 514/479; 564/197; 564/193; 935/54
[58] Field of Search .................................... 514/478, 479, 514/613, 626; 935/54; 564/123, 197, 193

[56] References Cited

U.S. PATENT DOCUMENTS

| | | | |
|---|---|---|---|
| 4,897,355 | 1/1990 | Eppstein et al. | 435/240.2 |
| 5,171,678 | 12/1992 | Behr et al. | 435/172.3 |
| 5,283,185 | 2/1994 | Epand et al. | 435/172.3 |
| 5,693,622 | 12/1997 | Wolff et al. | 514/44 |

FOREIGN PATENT DOCUMENTS

| | | |
|---|---|---|
| WO 92/02258 | 2/1992 | WIPO . |
| WO 92/09705 | 6/1992 | WIPO . |
| WO 97/03939 | 2/1997 | WIPO . |

OTHER PUBLICATIONS

Clivio, et al., Synthesis and Purification of Oligonucleotides Containing Sulfur Substituted Nucleobases: 4–Thiouracil, 4–Thiothymine and 6–Mercaptopurine; Tetrahedron Letters, 33(1):65–68 (1992).
Clivio, et al., Synthesis of Dinucleoside Phosphates Containing Sulfur Substituted Nucleobases: 4–Thiouracil, 4–Thiothymine and 6–Mercaptopurine; Tetrahedron Letters, 33(1)69–72 (1992).
Connolly, et al., Synthesis and properties of oligonucleotides containing 4–thiothymidine, 5–methyl–2–pyrimidinone–1β–D(2'deoxyriboside) and 2–thiothymidine, Nucleic Acids Research, 17(13):4957–4974 (1989).
Felgner, et al., Enhanced Gene Delivery and Mechanism Studies with a Novel Series of Cationic Lipid Formulations, J. Biol. Chem. 269(4):2550–2561 (1994).
Felgner, et al., Lipofection: A highly efficient, lipid–mediated DNA–transfection procedure; Proc. Natl. Acad. Sci. USA, 84:7413–7417 (1987).
Fukunaga, et al., Liposome Entrapment Enhances the Hypocalcemic Action of Parenterally Administered Calcitonin; Endocrinology, 115(2):757–761 (1984).
Gao, et al., A Novel Cationic Lipoxome Reagent for Efficient Transfection of Mammalian Cells; Biochem. and Biophys. Res. Comm., 179(1)280–285 (1991).
Gershon, et al., Mode of Formation and Structural Features of DNA–Cationic Liposome Complexes Used for Transfection; Biochemistry 32:7143–7151 (1993).
Kim, et al., Preparation of Multivesicular Liposomes; Biochimica et Biophysica Acta, 728:339–348 (1983).
Mayer, et al., vesicles of variable sizes produced by a rapid extrusion procedure; Biochimica et Biophysica Acta, 858:161–168 (1986).
Mayhew, et al., Characterization of liposomes prepared using a microemulsifier; Biochimica et Biophysic Acta, 775:169–174 (1984).
Nabel, et al., Gene Transfer in Vivo with DNA–Liposome Complexes: Lack of Autoimmunity and Gonadal Localization; Human Gene Therapy, 3:649–656 (1992).
Nabel, et al., Direct gene transfer with DNA–liposome complexes in melanoma: Expression, biologic activity, and lack of toxicity in humans; Proc. Natl. Acad. Sci. USA, 90:11307–11311 (1993).
Nikiforov, et al., 5'–O–(4,4"Dimethoxytrityl)–4–Thiocyanatothymidine: A Useful Intermediate for the Preparation of Various 4–Substituted Thymidine Analogues; Tetahedron Letters, 32(22):2505–2508 (1991).
Nikiforov, et al., Straightforward Preparation and Use in Oligodeoxynucleotide Synthesis of 5'–O–(4,4"Dimethoxytrityl)–4–[S–(2–Cyanoethyl)]–Thiothymidine; Tetrahedron Letters, 33(17):2379–2382 (1992).
Olson et al., Preparation of Liposomes of Defined Size Distribution by Extrusion Through Polycarbonate Membranes; Biochimica et Biophysica Acta, 557:9–23 (1979).
Strauss, et al., Molecular complemantation of a collagen mutation in mammalian cells using yeast artificial chromosomes; EMBO Journal 11(2):417–422 (1992).
Szoka, et al., Procedure for preparation of liposomes with large internal aqueous space and high capture by reverse–phase evaporation; Proc. Natl. Acad. Sci. USA, 75(9):4194–4198 (1978).
Wagner, et al., Antisense Gene Inhibition by Oligonucleotides Containing C–5 Propyne Pyrimidines; Science 260:1510–1513 (1993).
Xu, et al., Simple Synthesis of 4–Thiothymidine, 4–Thiouridine and 6–Thio–2'–deoxyguanosine; Tetrahedron Letters, 32(24):2817–2820(1991).
Zhou, et al., Lipophilic polylysines mediate efficient DNA transfection in mammalian cells; Biochimica et Biophysica Acta, 1065:8–14 (1991).

*Primary Examiner*—Jon P. Weber
*Attorney, Agent, or Firm*—Knobbe, Martens, Olson & Bear, LLP

[57] ABSTRACT

The present invention provides amide-based oligomeric cationic lipids. The present invention further provides compositions of these amide-based cationic lipids with anionic macromolecules, methods for interfering with protein expression in a cell utilizing these compositions and a kit for preparing the same.

37 Claims, 2 Drawing Sheets

Lipid P

AMIDE-BASED OLIGOMERIC CATIONIC LIPIDS

TECHNICAL FIELD

The present invention is directed to oligomeric cationic lipid compounds useful in lipid aggregates for the delivery of macromolecules into cells.

BACKGROUND AND INTRODUCTION TO THE INVENTION

Some bioactive substances do not need to enter cells to exert their biological effect, because they operate either by acting on cell surfaces through cell surface receptors or by interacting with extracellular components. However, many natural biological molecules and their analogues, such as proteins and polynucleotides, or foreign agents, such as synthetic molecules, which are capable of influencing cell function at the subcellular or molecular level are preferably incorporated within the cell in order to produce their effect. For these agents the cell membrane presents a selective barrier which may be impermeable to them.

While these membranes serve a protective function by preventing entry of toxic substances, they can also prevent passage of potentially beneficial therapeutic agents into the body. This protective function is influenced by the complex composition of the cell membrane which includes phospholipids, glycolipids, cholesterol, and intrinsic and extrinsic proteins, as well as by a variety of cytoplasmic components. Interactions between these structural and cytoplasmic cell components and their response to external signals make up transport processes responsible for the membrane selectivity exhibited within and among cell types.

Successful intracellular delivery of agents not naturally taken up by cells has been achieved to some extent by exploiting natural delivery vehicles, such as viruses, that can penetrate a cell's membrane or are taken up by the cell's natural transport mechanisms or by natural process of intracellular membrane fusion. (Duzgunes, N., *Subcellular Biochemistry* 11:195–286, 1985).

The membrane barrier may be overcome in the first instance by viral infection or transduction. Various techniques for introducing the DNA or mRNA precursors of bioactive peptides into cells include the use of viral vectors, such as recombinant vectors and retroviruses, which have the inherent ability to penetrate cell membranes. However, the use of such viral agents to integrate exogenous DNA into the chromosomal material of the cell carries a risk of damage to the genome and the possibility of inducing malignant transformation.

Another aspect of this approach which restricts its use in vivo is that the integration of DNA into the genome accomplished by these methods implies a loss of control over the expression of the peptide it encodes, so that transitory therapy is difficult to achieve and potential unwanted side effects of the treatment could be difficult or impossible to reverse or terminate.

The membrane barrier may also be overcome by associating these agents in complexes with lipid formulations closely resembling the lipid composition of natural cell membranes. These lipids are able to fuse with the cell membranes, and in the process, the associated agents are delivered intracellularly. The structure of various types of lipid aggregates in formulations vary depending on a variety of factors which include composition and methods of forming the aggregate. Lipid aggregates include, for example, liposomes, unilamellar vesicles, multilamellar vesicles, micelles and the like, and may have particle sizes in the nanometer to micrometer range.

The lipids of these formulations may comprise an amphipathic lipid, such as the phospholipids of cell membranes, which form hollow lipid vesicles or liposomes in aqueous systems either spontaneously or by mechanical agitation. This property can be used to entrap the agent to be delivered within the liposomes. In other applications, the agent of interest can be incorporated into the lipid vesicle as an intrinsic membrane component, rather than entrapped in the hollow aqueous interior.

Liposomes have been utilized as in vivo delivery vehicles and some encouraging results were obtain when this approach was applied to intracellular expression of DNA (Mannino, R. J. and Fould-Fogerite, S., *Biotechniques* 6:682–690, 1988; Itani, T. et al. *Gene* 56:267—276. 1987; Nicolau, C. et al. *Meth. Enz.* 149:157–176, 1987; Straubinger, R. M. and Papahadjopoulos, D. *Meth. Enz.* 101:512–527, 1983; Wang, C. Y. and Huang, L., *Proc. Natl. Acad. Sci. USA* 84:7851–7855, 1987; however, the methodology has fundamental problems. An important drawback to the use of this type of aggregate as a cell delivery vehicle is that the liposome has a negative charge that reduces the efficiency of binding to a negatively charged target cell surface. Consequently, the liposome is often taken up by the cell phagocytically. Phagocytized liposomes are delivered to the lysosomal compartment, where polynucleotides are subjected to the action of digestive enzymes and degraded, which leads to low efficiency of expression.

A major advance in this area was the discovery that a positively charged synthetic cationic lipid, N-[1-(2,3-dioleyloxy) propyl]-N,N,N-trimethylammonium chloride (DOTMA), in the form of liposomes, or small vesicles, could interact spontaneously with DNA to form lipid-DNA complexes which are capable of fusing with the negatively charged lipids of the cell membranes of tissue culture cells, resulting in both uptake and expression of the DNA (Felgner, P. L. et al. *Proc. Natl. Acad. Sci., USA* 8:7413–7417, 1987 and U.S. Pat. No. 4,897,355 to Eppstein, D. et al.). Others have successfully used a DOTMA analogue, 1,2-bis (oleoyloxy)-3-(trimethylammonia) propane (DOTAP) in combination with a phospholipid to form DNA-complexing vesicles.

Lipofectin™ (Bathesda Research Laboratories, Gaithersburg, Md.) is an effective agent for the delivery of highly anionic polynucleotides into living tissue culture cells that comprises positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional polynuleotide into, for example, tissue culture cells.

Although the use of known cationic lipids overcomes some of the problems associated with conventional liposome technology for polynucleotide delivery in vitro, problems related to both in vitro and in vivo applications remain. Cationic lipids such as DOTMA are toxic to tissue culture cells and are expected to accumulate in the body due to their poorly metabolized ether bonds.

Another commercially available cationic lipid, 1,2-bis (oleoyloxy)-3,3-(trimethylammonia)propane ("DOTAP") differs from DOTMA in that the oleoyl moieties are linked by ester, rather than ether linkages. However, DOTAP is reported to be more readily degraded by target cells leading to low efficiency of delivery.

Other reported cationic lipid compounds include those which have been conjugated to a variety of moieties including, for example, carboxyspermine which has been conjugated to one of two types of lipids and includes compounds such as 5-carboxyspermylglycine dioctaoleoylamide ("DOGS") and dipalmitoyl-phosphatidylethanolamine 5-carboxyspermyl-amide ("DPPES") (See, e.g. Behr et al., U.S. Pat. No. 5,171,678).

Another cationic lipid conjugate includes derivatization of the lipid with cholesterol ("DC-Chol") which has been formulated into liposomes in combination with DOPE. (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions.

However, of the cationic lipids which have been proposed for use in delivering agents to cells, no particular cationic lipid has been reported to work well with a wide variety of cell types. Since cell types differ from one another in membrane composition, different cationic lipid compositions and different types of lipid aggregates may be effective for different cell types, either due to their ability to contact and fuse with particular target cell membranes directly or due to different interactions with intracellular membranes or the intracellular environment.

Thus, there remains a need for improved cationic lipids which are capable of delivering macromolecules to a wide variety cell types with greater efficiency.

SUMMARY OF THE INVENTION

The present invention provides compositions of novel oligomeric cationic lipids, conjugates of these lipids with other molecules, and aggregates of these cationic lipids with anionic macromolecules. The invention further provides methods for their synthesis, methods of use and a kit for delivering anionic macromolecules using these novel cationic lipids.

In one aspect of the present invention provides oligomeric cationic lipids having the structure:

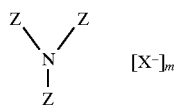

wherein Z is

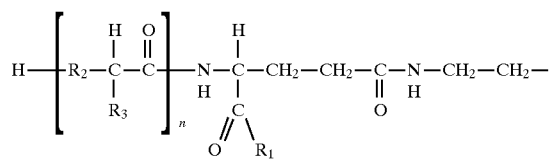

wherein
(a) n is 0, 1 or 2;
(b) $R_1$ is hydroxy, a glyceryl moiety or a lipophilic moiety;

(c) $R_2$ is
  (i) —NH-[alk$_1$—NH]$_{n1}$-
    wherein n1 is an integer from 0 to 2 and alk$_1$ is an alkylene group of 2 to 6 carbon atoms;
  (ii) -[W$_1$]$_{n2}$-
    wherein n2 is an integer from 0 to 3 and each $W_1$ is an independently selected amino acid residue;
  (iii) —N(R$_4$) (alk$_2$)-
    wherein $R_4$ is hydrogen, alkyl of 1 to 18 carbon atoms optionally mono-, di- or tri-substituted with $Y_1$, $Y_2$ and/or $Y_3$; alkenyl of 2 to about 12 carbon atoms, aryl of about 6 to about 14 carbon atoms and aralkyl of about 7 to about 15 carbon atoms and alk$_2$ is a straight chained or branched chain alkylene group of 1 to 18 carbon atoms optionally mono-, di- or tri-substituted with $Y_1$, $Y_2$ and/or $Y_3$; where $Y_1$, $Y_2$ and $Y_3$ are independently selected from the group consisting of arylamine of 5 to about 10 carbon atoms, aralkylamine of 5 to about 10 carbon atoms, heterocyclic amine, fluorine, a guanidinium moiety, an amidinium moiety, —NH$_2$, —NHR$_{10}$, —NR$_{10}$R$_{11}$ and —N(R$_{10}$R$_{11}$R$_{12}$) wherein R$_{10}$, R$_{11}$ and R$_{12}$ are as defined hereinbelow;

(d) $R_3$ is
  (i) —NH-[alk$_3$]$_{n3}$—H wherein n3 is an integer from 0 to 4 and alk$_3$ is an alkylene group of 2 to 6 carbon atoms;
  (ii) -[W$_2$]$_{n4}$H wherein n4 is an integer from 0 to 3 and each $W_2$ is an independently selected amino acid residue;
  (iii) a negatively charged group selected from the group consisting of -alk$_4$C (O)O$^-$; -alk$_4$—S(O$_2$) O$^-$; -alk$_4$P (O) (O$^-$)$^{O-}$ and -alk$_4$OP(O) (O$^-$) (O$^-$)
    wherein alk$_4$ is an alkylene group of 1 to 6 carbon atoms;
  (iv) heterocyclo of 4 to about 10 ring atoms with the ring atoms selected from carbon and heteroatoms, wherein the heteroatoms are selected from the group consisting of oxygen, nitrogen and S(O)$_i$, wherein i is 0, 1 or 2;
  (v) alkyl of 1 to about 12 carbon atoms optionally substituted with a substituent selected from fluoro, a guanidinium moiety, an amidinium moiety, —NH$_2$, —NHR$_{10}$, —NR$_{10}$R$_{11}$ or NR$_{10}$R$_{11}$R$_{12}$ wherein each of R$_{10}$, R$_{11}$ and R$_{12}$ is independently selected from alkyl of 1 to about 12 carbon atoms, alkyl of 1 to about 12 carbon atoms substituted with 1 to about 25 fluorine atoms and alkenyl of 2 to about 12 carbon atoms; or
  (vi) W$_3$—(CH$_2$)$_t$—NH—(CH$_2$)$_q$- wherein t and q are independently selected integers from 2 to 6 and $W_3$ is a guanidinium moiety, an amidinium moiety, —NH$_2$, —NHR$_{10}$,—NR$_{10}$R$_{11}$ or —NR$_{10}$R$_{11}$,R$_{12}$ wherein R$_{10}$, R$_{11}$ and R$_{12}$ are as defined hereinabove (e) X$^-$ is an anion or a polyanion; and
(f) m is an integer selected such that [X$^-$] is equal to the positive charge of the lipid.

Also included within the scope of our invention is a lipid of the above without the counter ion [X$^-$]$_m$.

According to one aspect of the invention, $R_1$, is a lipophilic moiety. Suitable lipophilic moieties include, but are not limited to, a symmetrical branched alkyl or alkenyl moiety of about 10 to about 50 carbon atoms, a unsymmetrical branched alkyl or alkenyl moiety of about 10 to about 50 carbon atoms, a steroidyl moiety (such as cholesteryl), a glyceryl moiety, the group —OCH(R$_6$R$_7$) wherein $R_6$ and $R_7$ are independently selected alkyl groups of about 10 to about 50 carbon atoms, —N (R$_8$,R$_9$), wherein $R_8$ and $R_9$ are independently selected alkyl or alkenyl groups of about 10 to about 50 carbon or taken together form a cyclic amine group of about 4 to about 10 carbon atoms.

Where $R_2$ is —$N(R_4)$ ($alk_2H$) and $R_4$ is a substituted alkyl moiety of 1 to about 18 carbon atoms, the substituted alkyl moiety may be substituted with 1 to 3 substituents selected from an arylamine moiety of about 5 to about 10 carbon atoms, an aralkylamine of about 5 to 10 carbon atoms, a heterocyclic amine, F, a guanidinium moiety, an amidinium moiety, —$NH_2$, —$NHR_{10}$, —$N(R_{10}R_{11})$, and —$N(R_{10}R_{11}, R_{12})$ wherein $R_{10}$, $R_{11}$, and $R_{12}$ are as defined herein above.

Suitable anions, X, include pharmaceutically acceptable anions and polyanions. Preferred pharmaceutically acceptable anions and polyanions include trifluoroacetates.

In addition, according to another aspect, the invention provides compositions comprising a anionic macromolecule and a lipid of the present invention. Suitable anionic macromolecules include an expression vector capable of expressing a polypeptide in a cell and an Oligomer, more preferably DNA or RNA.

Particular preferred lipids of the present invention include but are not limited to the following structures:

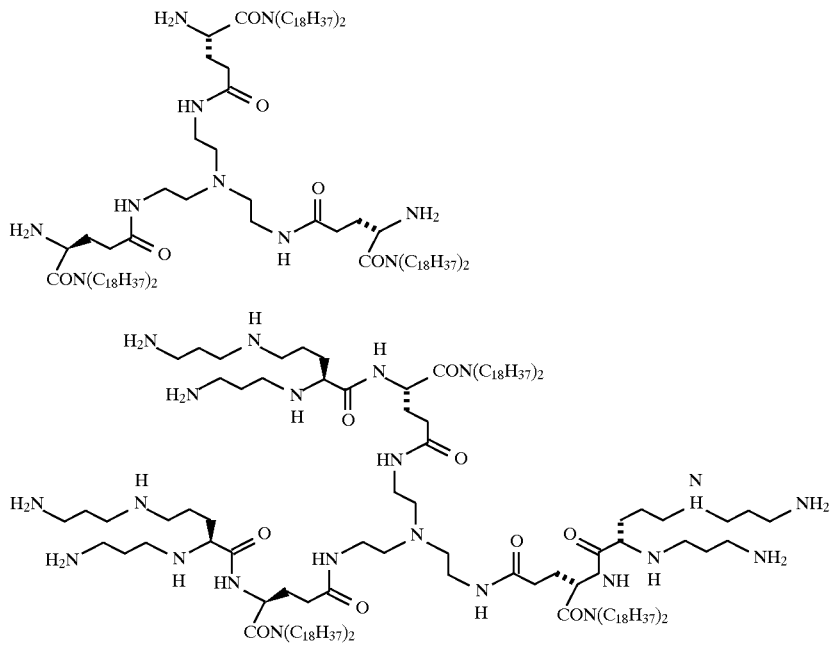

Preferred $R_2$ groups include —$NH[alk,NH]_{n1}$—H wherein n1 is 0 or 1. Preferred $alk_1$ groups include —$(CH_2)_3$-.

When $R_2$ is -$[W_1]_{n1}$, suitable $W_1$ groups include amino acid residues optionally substituted with an alkyl of 1 to about 12 carbon atoms or wherein the amino group(s) is substituted to form a secondary, tertiary, or quaternary amine with an alkyl moiety of 1 to about 12 carbon atoms. Preferred amino acid residues include lysine, arginine, histidine, ornithine, tryptophane, phenylalanine, or tyrosine. Alternatively $W_1$ may be an amino acid analog. Suitable amino acid analogs include 3-carboxyspermidine, 5-carboxyspermidine, 6-carboxyspermine or monoalkyl, dialkyl, or peralkyl substituted derivatives thereof which are substituted on one or more amine nitrogens with a alkyl group of 1 to about 12 carbon atoms.

Where $R_2$ is -$[W_1]_{n2}$H and n2 is 2 or 3, each $W_1$ may be independently selected, and $R_2$ may include natural amino acids, unnatural amino acids or a combination of natural and unnatural amino acids.

When $R_4$ is a substituted alkyl group, suitable substitutions include the following substituents —F, guanidinium moiety, amidinium moiety, —$NH_2$, —$NHR_{10}$, —$N(R_{10}R_{11})$, and —$N(R_{10}R_{11}R_{12})$ wherein $R_{10}$, $R_{11}$ and $R_{12}$ as defined herein above.

In an alternate aspect, the present invention provides compositions which comprise a mixture of a lipid of the present invention mixed with a second lipid. Preferred are compositions which comprise a compound of the present invention and a second lipid such as those described in PCT/US96/09476, and particularly preferred second lipids include Lipid P as depicted in FIG. 2. Preferred lipids of the present invention include Lipids 3—3, depicted in FIG. 1. The lipids may be present in a variety of ratios, preferably from about 1:20 to about 20:1. Preferably the lipids are present in a 1:1 weight:weight mixture. Particularly preferred is a mixture of 3—3 and Lipid P.

The invention further provides methods for delivering a anionic macromolecule into a cell by contacting said cell with a composition of the present invention. Also provided are methods for interfering with the expression of a preselected in a cell by contacting said cell with a composition of the present invention wherein the anionic macromolecule is an Oligomer having a nucleoside base sequence which is substantially complimentary to an RNA or DNA sequence in the cell that encodes the preselected protein.

Definitions

In accordance with the present invention and as used herein, the following terms are defined with the following meanings, unless explicitly otherwise.

The term "amino acid" refers to both natural and unnatural amino acids in either their L- or D-forms. Natural amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. For example, unnatural amino acids include, but are not limited to azetidinecarboxylic acid, 2-aminoadipic acid, 3-aminoadipic acid, β-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4diaminoisobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methylisoleucine, N-methylvaline, norvaline, norleucine, ornithine and pipecolic acid.

The term "amino acid residue" refers to —NH—CH(R)—CO—, wherein R is the side chain group distinguishing each amino acid. For cyclic amino acids, the residue is

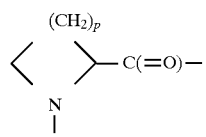

wherein p is 1, 2 or 3 representing the azetidinecarboxylic acid, proline or pipecolic acid residues, respectively.

The term "alkyl" refers to saturated aliphatic groups including straight-chain, branched-chain and cyclic groups.

The term "alkenyl" refers to unsaturated hydrocarbyl group which contain at lest one carbon-carbon double bond and includes straight-chain, branched-chain and cyclic groups.

The term "aryl" refers to aromatic groups which have at least one ring having a conjugated pi electron system and includes carbocyclic aryl, heterocyclic aryl and biaryl groups, all of which may be optionally substituted.

The term "aralkyl" refers to an alkyl group substituted with an aryl group. Suitable aralkyl groups include benzyl, picolyl, and the like, all of which may be optionally substituted.

The term "aralkenyl" refers to an alkenyl group substituted with an aryl group. Suitable aralkenyl groups include styrenyl and the like, all of which may be optionally substituted.

The term "alkoxy" refers to the group —OR wherein R is alkyl.

The term "alkenyloxy" refers to the group —O—R wherein R is alkenyl.

The term "aryloxy" refers to the group —O—R wherein R is aryl.

The term "aralkyloxy" refers to the group —O—R wherein R is aralkyl.

The term "alkylene" refers to a divalent straight chain or branched chain saturated aliphatic radical.

The term "alkylenecarboxy" refers to the group -alk—COOH where alk is alkylene.

The term "carboxamide" refers to the group —C(O)—NH$_2$.

The term "alkylenecarboxamide" refers to the group -alk—C(O)NH$_2$ where alk is alkylene.

The term "alkylenehydroxy" refers to the group -alk—OH wherein alk is alkylene.

The term "methylene" refers to —CH$_2$—.

The term "perfuoroalkyl" refers to an alkyl group wherein each hydrogen is replaced by a fluoro. Suitable perfluoroalkyl groups include perfluoromethyl (having the structure of CF$_3$—) and perfluroethyl (having the structure of CF$_3$—CF$_2$—) and the like.

The term "lipophilic moiety" refers to a moiety has one or more of the following characteristics: is water insoluble, is soluble in non-polar solvent, favors octanol in octanol/water partition measurements, or is compatible with lipid bilayers and may be bilayer forming.

The term "aralkylamine" refers to an alkylamine substituted with an aryl group. Suitable aralkyl groups include benzyl and other alkyl substituted heterocycles and the like, all of which may be optionally substituted.

The term "aralkyl" refers to an alkyl group substituted with an aryl group. Suitable aralkyl groups include benzyl and other alkyl substituted heterocycles and the like, all of which may be optionally substituted.

The term "heterocyclic" refers to a group having from 1 to 4 heteroatoms as ring atoms in the aromatic ring and the remainder of the ring atoms are carbon atoms. Suitable heteroatoms include but are not limited to oxygen, nitrogen, sulfur, and selenium.

The term "heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

The term "steroidyl" refers to a group of lipids that contain a hydrogenated cyclopentanoperhydrophenanthrene ring system. A prefered steroidyl moiety is cholesteryl.

The term "glyceryl" refers to a mono-, di-, or trivalent radical formed by removal of a hydrogen from one, two, or three of the hydroxyl groups of a glycerol molecule, which is a trihydric sugar alcohol of the formula CH$_2$OHCHOHCH$_2$OH.

The term "arylamine" refers to aromatic groups that have at least one ring having a conjugated pi electron system and includes carbocyclic aryl, heterocyclic aryl, and biaryl groups, all of which are substituted with an amine.

The term "substantially complementary" refers to the Watson-Crick base pairing of the nucleosides of the target oligonucleotide sequence with the nucleosides of the oligomer provided by this invention. It is preferable that the sequence of the oligomer have sufficient complimentarity to bind and interfere with gene expression of the target oligonucleotide.

Preferably the oligomer is at least 50% complimentary to the target oligonucleotide, more preferably at least 70% and most preferably at least 80%.

The term "amidinium" refers to the substituent of amidine which includes any compound having the monovalent group —C(NH)(NH$_2$).

The term "oligonucleoside" or "Oligomer" refers to a chain of nucleosides that are linked by internucleoside linkages that is generally from about 4 to about 100 nucleosides in length, but which may be greater than about 100 nucleosides in length. They are usually synthesized from nucleoside monomers, but may also be obtained by enzymatic means. Thus, the term "oligomer" refers to a chain of oligonucleosides that have internucleosidyl linkages linking the nucleoside monomers and, thus, includes oligonucleotides, nonionic oligonucleoside alkyl-and aryl-phosphonate analogs, alkyl-and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a morpholino linkage, a sulfamate linkage, a silyl linkage, a carbamate linkage, an amide linkage, a guanidine linkage, a nitroxide linkage or a substituted hydrazine linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "polyfunctional linkers" refers to any polymer containing reactive atoms or reactive side chains that can be covalently linked to cationic lipid subunits as those described in the present invention, for example polyfunctional linkers may include but are not limited to polyethylenamine, polypropylenamine, polybutylenamine, polyethylene glycol, oxidized dextran, polyacrylamide, polylysine or a polypeptide derivative having reactive side chains. Such polypeptide derivative reactive side chains include for example the amino acid side chains of lysine, arginine, methionine, histidine, glutamine, asparagine, serine, threonine, glutamate and aspartate.

The term "lipid aggregate" includes liposomes of all types both unilamellar and multilamellar as well as micelles and more amorphous aggregates of cationic lipid or lipid mixed with amphipathic lipids such as phospholipids.

The term "target cell" refers to any cell to which a desired compound is delivered, using a lipid aggregate as carrier for the desired compound.

The term "transfection" refers to the delivery of expressible nucleic acid to a target cell, such that the target cell is rendered capable of expressing said nucleic acid. It will be understood that the term "nucleic acid" includes both DNA and RNA without regard to molecular weight, and the term "expression" means any manifestation of the functional presence of the nucleic acid within the cell, including without limitation, both transient expression and stable expression.

The term "delivery" refers to a process by which a desired compound is transferred to a target cell such that the desired compound is ultimately located inside the target cell or in, or on the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

DETAILED DESCRIPTION OF THE INVENTION

Figure 1:
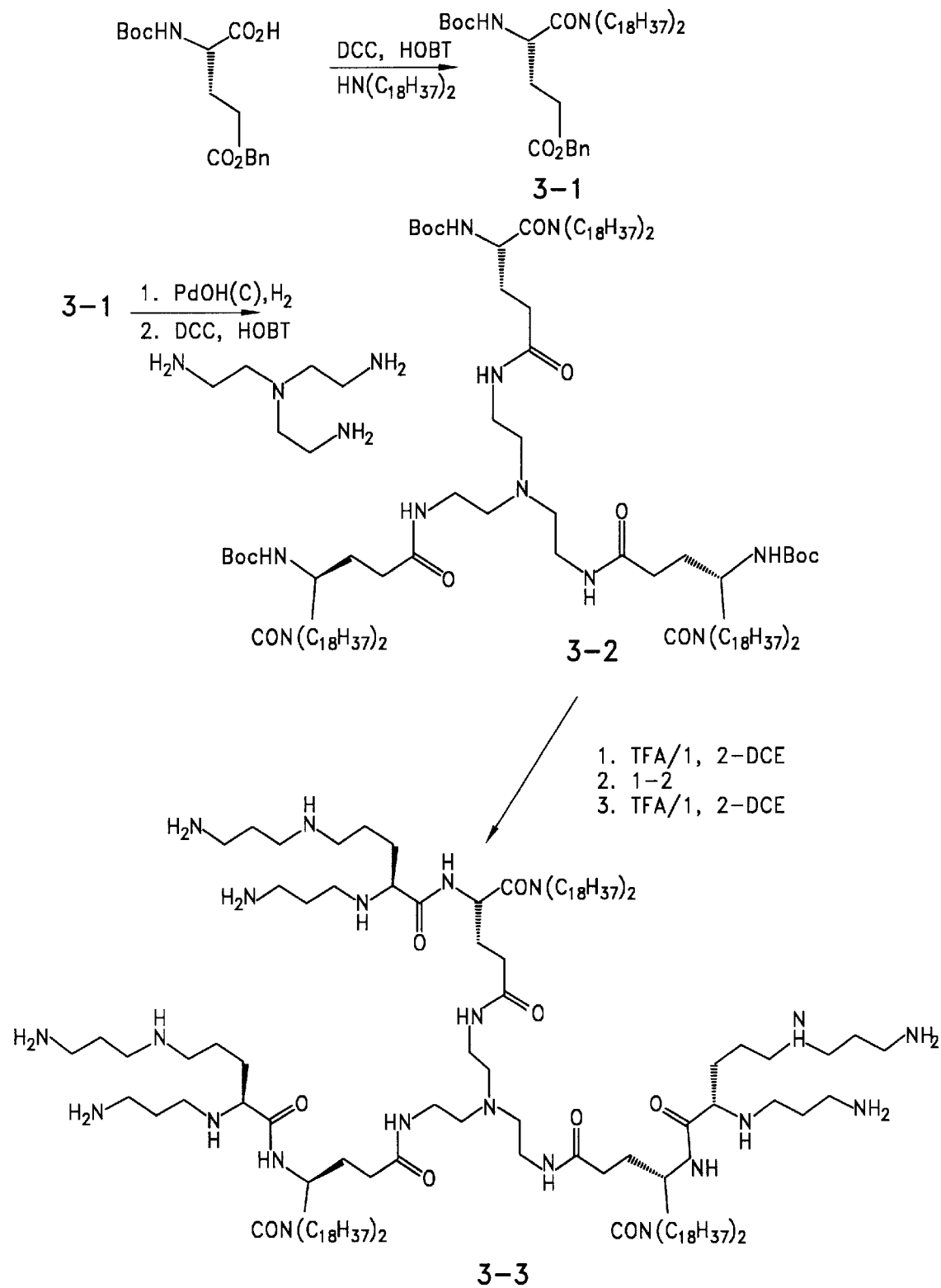
FIG. 1 is a schematic representation of the synthesis of compound 3—3.
Figure 2:
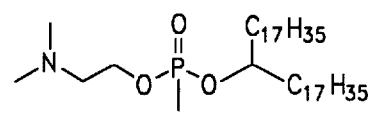
FIG. 2 depicts the structure of Lipid P. Lipid P is described in PCT/US96/09478.

All references cited below are hereby incorporated by reference in their entirety.

The generic structure of functionally active cationic lipids requires three contiguous moieties, e.g. cationic-head-group, linker, and lipid-tail group. While a wide range of structures can be envisioned for each of the three moieties, it has been demonstrated that there is no a priori means to predict which cationic lipid will successfully transfect anionic macromolecules into a particular cell line. The property of a cationic lipid to be formulated with an anionic macromolecule which will then successfully transfect a cell line is empirical. We demonstrate the abilities of novel cationic lipids which are chemically linked into multimeric constructions to enhance the uptake of macromolecules.

The novel oligomeric cationic lipids of the present invention have the general structure:

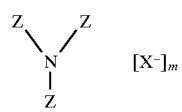

wherein Z is

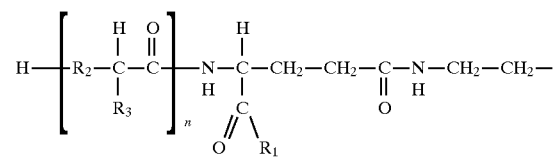

and $R_1$, $R_2$, $R_3$ and n are as set forth hereinabove.

The counterion represented by $X^-$ is an anion or a polyanion that binds to the positively charged groups present on the oligomeric cationic lipid via charge-charge interactions. When these cationic lipids are to be used in vivo the anion or polyanion should be pharmaceutically acceptable.

m is an integer indicating the number of anions or polyanions associated with the cationic lipid. In particular this integer ranges in magnitude from 0 to a number equivalent to the positive charge(s) present on the lipid.

n is an integer indicating the number of repeating units enclosed by the brackets. Preferably n is an integer from 0 to 2.

The cationic lipids of the present invention include enantiomeric isomers resulting from any or all asymmetric atoms present in the lipid. Included in the scope of the invention are racemic mixtures, diastereomeric mixtures, optical isomers or synthetic optical isomers which are isolated or substantially free of their enantiomeric or diasteriomeric partners. The racemic mixtures may be separated into their individual, substantially optically pure isomers by techniques known in the art, such as, for example, the separation of diastereomeric salts formed with optically active acid or base adjuncts followed by conversion back to the optically active substances. In most instances, the desired optical isomer is synthesized by means of stereospecific reactions, beginning with the appropriate stereoisomer of the desired starting material. Methods and theories used to obtain enriched and resolved isomers have been described (Jacques et al., "Enantiomers, Racemates and Resolutions." Kreiger, Malabar, FL, 1991).

Exemplary cationic lipids of the invention have the structures shown in the Summary of the Invention above.

Preferred Compositions and Formation of Lipid Aggregates

The cationic lipids form aggregates with anionic or polyanionic macromolecules such as oligonucleotides, oligomers, peptides, or polypeptides through attraction between the positively charged lipid and the negatively charged anionic macromolecule. The aggregates may comprise multilamellar or unilamellar liposomes or other particles. Hydrophobic interactions between the cationic lipids and the hydrophobic substituents in the anionic or polyanionic macromolecule such as aromatic and alkyl moieties may also facilitate aggregate formation. Cationic lipids have been shown to efficiently deliver nucleic acids and peptides into cells and thus are suitable for use in vivo or ex vivo.

Cationic lipid-anionic macromolecule aggregates may be formed by a variety of methods known in the art. Representative methods are disclosed by Felgner et al., supra; Eppstein et al. supra; Behr et al. supra; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization is used when consistently small (50 to 200 nm) and relatively uniform aggregates are desired (Mayhew, supra). In general, aggregates may be formed by preparing lipid particles consisting of either (1) a cationic lipid of the invention or (2) a cationic lipid mixed with a colipid, followed by adding a anionic macromolecule to the lipid particles at about room temperature (about 18° to 26° C.). In general, conditions are chosen that are not conducive to deprotection of protected groups. The mixture is then allowed to form an aggregate over a period of about 10 minutes to about 20 hours, with about 15 to 60 minutes most conveniently used. The complexes may be formed over a longer period, but additional enhancement of transfection efficiency will not usually be gained by a longer period of complexing. Colipids may be natural or synthetic lipids having no net charge or a positive or negative charge. In particluar, natural colipids that are suitable for preparing lipid aggregates with the cationic lipids of the present invention are dimyristoylphosphatidylethanolamine, dipalmitoylphosphatidylethanolamine, palmitoyloleolphosphatidylethanolamine, cholesterol, distearoyalphosphatidylethanolamine, phosphatidylethanolamine, phosphatidylethanolamine covalently linked to polyethylene glycol and mixtures of these colipids.

The optimal cationic lipid:colipid ratios for a given cationic lipid is determined by mixing experiments to prepare lipid mixtures for aggregation with a anionic macromolecule using cationic lipid:colipid ratios between about 1:0.1 and 1:10. Methods to determine optimal cationic lipid:colipid ratios have been described (see, Felgner, infra). Each lipid mixture is optionally tested using more than one oligonucleotide-lipid mixture having different nucleic acid:lipid molar ratios to optimize the oligonucleotide:lipid ratio.

Suitable molar ratios of cationic lipid:colipid are about 0.1:1 to 1:0.1, 0.2:1 to 1:0.2, 0.4:1 to 1:0.4, or 0.6:1 to 1:0.6. Lipid particle preparation containing increasing molar proportions of colipid have been found to enhance oligonucleotide transfection into cells with increasing colipid concentrations.

In addition, the cationic lipids can be used together in admixture, or different concentrations of two or more cationic lipids in admixture, with or without colipid.

Liposomes or aggregates may be conveniently prepared by first drying the lipids in solvent (such as chloroform) under reduced pressure. The lipids may then be hydrated and converted to liposomes or aggregates by adding water or low ionic strength buffer (usually less than about 200 mM total ion concentration) followed by agitating (such as vortexing and/or sonication) and/or freeze/thaw treatments. The size of the aggregates or liposomes formed range from about 40 nm to 600 nm in diameter.

The amount of an oligonucleotide delivered to a representative cell by at least some of the cationic lipids was found to be significantly greater than the amount delivered by commercially available transfection lipids. The amount of oligonucleotide delivered into cells was estimated to be about 2- to 100-fold greater for the cationic lipids of the invention based on the observed fluorescence intensity of transfected cells after transfection using a fluorescently labeled oligonucleotide. The cationic lipids described herein also transfect some cell types that are not detectably transfected by commercial lipids. Functionality of cationic lipid-DNA aggregates was demonstrated by assaying for the gene product of the exogenous DNA. Similarly, the functionality of cationic lipid-oligonucleotide aggregates were demonstrated by antisense inhibition of a gene product.

The cationic lipids described herein also differed from commercially available lipids by efficiently delivering an oligonucleotide into cells in tissue culture over a range of cell confluency from about 50–100%. Most commercially available lipids require cells that are at a relatively narrow confluency range for optimal transfection efficiency. For example, Lipofectin™ requires cells that are 70–80% confluent for transfecting the highest proportion of cells in a population. The cationic lipids described herein may be used to transfect cells that are about 10–50% confluent, however, it is preferable to transfect at a confluency of 60% to 100% for optimal efficiency. Confluency ranges of 60–95% or 60–90% are thus convenient for transfection protocols with most cell lines in tissue culture.

The cationic lipid aggregates were used to transfect cells in tissue culture and the RNA and the DNA encoded gene products were expressed in the transfected cells.

The cationic lipid aggregates may be formed with a variety of macromolecules such as oligonucleotides and oligomers. Oligonucleotides used in aggregate formation may be single stranded or double stranded DNA or RNA, oligonucleotide analogs, or plasmids.

Preferred Anionic Macromolecules

In general, relatively large oligonucleotides such as plasmids or mRNAs will carry one or more genes that are to be expressed in a transfected cell, while comparatively small oligonucleotides will comprise (1) a base sequence that is complementary (via Watson Crick or Hoogsteen binding) to a DNA or RNA sequence present in the cell or (2) a base sequence that permits oligonucleotide binding to a molecule inside a cell such as a peptide, protein, or glycoprotein. Exemplary RNAs include ribozymes and antisense RNA sequences that are complementary to a target RNA sequence in a cell.

An oligonucleotide may be a single stranded unmodified DNA or RNA comprising (a) the purine or pyrimidine bases guanine, adenine, cytosine, thymine and/or uracil: (b) ribose or deoxyribose; and (c) a phosphodiester group that linkage adjacent nucleoside moieties. oligonucleotides typically comprise 2 to about 100 linked nucleosides. Typical oligonucleotides range in size from 2–10, 2–15, 2–20, 2–25, 2–30, 2–50, 8–20, 8–30 or 2–100 linked nucleotides. Oligonucleotides are usually linear with uniform polarity and, when regions of inverted polarity are present, such regions comprise no more than one polarity inversion per 10 nucleotides. One inversion per 20 nucleotides is typical. Oligonucleotides can also be circular, branched or double-stranded. Antisense oligonucleotides generally will comprise a sequence of about from 8–30 bases or about 8–50 bases that is substantially complementary to a DNA or RNA base sequence present in the cell. The size of oligonucleotide that is delivered into a cell is limited only by the size of anionic macromolecules that can reasonably be prepared and thus DNA or RNA that is 0.1 to 1 Kilobase (Kb), 1 to 20 Kb, 20 Kb to 40 Kb or 40 Kb to 1,000 Kb in length may be delivered into cells.

Oligonucleotides also include DNA or RNA comprising one or more covalent modifications. Covalent modifications include (a) substitution of an oxygen atom in the phosphodiester linkage of an polynucleotide with a sulfur atom, a methyl group or the like, (b) replacement of the phosphodiester group with a nonphosphorus moiety such as —O—CH$_2$O—, —S—CH$_2$O— or —O—CH$_2$O—S, and (c) replacement of the phosphodiester group with a phosphate analog such as —O—P(S)(O)—O—, —O—P(S) (S)—O—, —O—P (CH$_3$) (O)—O or —O—P (NHR$_{10}$) (O)—O— where R$_{10}$ is alkyl of 1 to about 6 carbon atoms, or an alkyl ether of 1 to about 6 carbon atoms. Such substitutions may constitute from about 10% to 100% or about 20% to about 80% of the phosphodiester groups in unmodified DNA or RNA. Other modifications include substitutions of or on sugar moiety such as morpholino, arabinose 2'-fluororibose, 2'-fluoroarabinose, 2'-O-methylribose, or 2'-O-allylribose. Oligonucleotides and methods to synthesize them have been described (for example see: PCT/US90/03138, PCT/US90/06128, PCT/US90/06090, PCT/US90/06110, PCT/US92/03385, PCT/US91/08811, PCT/US91/03680, PCT/US91/06855, PCT/US91/01141, PCT/US92/10115, PCT/US92/10793, PCT/US93/05110, PCT/US93/05202, PCT/US92/04294, WO 86/05518, WO 89/12060, WO 91/08213, WO 90/15065, WO 91/15500, WO 92/02258, WO 92/20702, WO 92/20822, WO 92/20823, U.S. Pat. No. : 5,214,136 and Uhlmann Chem. Rev. 90:543, 1990).

The linkage between the nucleotides of the oligonucleotide may be a variety of moieties including both phosphorus-containing moieties and non phosphorus-containing moieties such as formacetal, thioformacetal, riboacetal and the like. A linkage usually comprises 2 or 3 atoms between the 5' position of a nucleotide and the 2' or 3' position of an adjacent nucleotide. However, other synthetic linkers may contain greater than 3 atoms.

The bases contained in the oligonucleotide may be unmodified or modified or natural or unnatural purine or pyrimidine bases and may be in the α or β anomer form. Such bases may be selected to enhance the affinity of oligonucleotide binding to its complementary sequence relative to bases found in native DNA or RNA. However, it is preferable that modified bases are not incorporated into an oligonucleotide to an extent that it is unable to bind to complementary sequences to produce a detectably stable duplex or triplex.

Exemplary bases include adenine, cytosine, guanine, hypoxanthine, inosine, thymine, uracil, xanthine, 2-aminopurine, 2,6-diaminopurine, 5-(4-methylthiazol-2-yl) uracil, 5-(5-methylthiazol-2-yl)uracil, 5-(4-methylthiazol-2-yl)cytosine, 5-(5-methylthiazol-2-yl)cytosine and the like. Other exemplary bases include alkylated or alkynylated bases having substitutions at, for example, the 5 position of pyrimidines that results in a pyrimidine base other than uracil, thymine or cytosine, (i.e., 5-methylcytosine, 5-(1-propynyl)cytosine, 5-(1-butynyl)cytosine, 5-(1-butynyl) uracil, 5-(1-propynyl)uracil and the like). The use of modified bases or base analogs in oligonucleotides have been previously described (see PCT/US92/10115; PCT/US91/08811; PCT/US92/09195; WO 92/09705; WO 92/02258; Nikiforov, et al., Tet. Lett. 33:2379, 1992; Clivio, et al., Tet. Lett. 33:65, 1992; Nikiforov, et al., Tet. Lett. 32:2505, 1991; Xu, et al., Tet. Lett. 32:2817, 1991; Clivio, et al., Tet. Lett. 33:69, 1992; and Connolly, et al., Nucl. Acids Res. 17:4957, 1989).

Use of Compositions and Lipid Aggregates

Aggregates may comprise oligonucleotides or oligomers encoding a therapeutic or diagnostic polypeptide. Examples of such polypeptides include histocompatibility antigens, cell adhesion molecules, cytokines, antibodies, antibody fragments, cell receptor subunits, cell receptors, intracellular enzymes and extracellular enzymes or a fragment of any of these. The oligonucleotides also may optionally comprise expression control sequences and generally will comprise a transcriptional unit comprising a transcriptional promoter, an enhancer, a transcriptional terminator, an operator or other expression control sequences.

Oligonucleotides used to form aggregates for transfecting a cell may be present as more than one expression vector. Thus, 1, 2, 3, or more different expression vectors may be delivered into a cell as desired. Expression vectors will typically express 1, 2, or 3 genes when transfected into a cell, although many genes may be present such as when a herpes virus vector or a artificial yeast chromosome is delivered into a cell. Expression vectors may further encode selectable markers (e.g. neomycin phosphotransferase, thymidine kinase, xanthine-guanine phosphoribosyl-transferase, and the like) or biologically active proteins such as metabolic enzymes or functional proteins (e.g. immunoglobulin genes, cell receptor genes, cytokines (e.g. IL-2, IL-4, GM-CSF, γ-INF, and the like)), or genes that encode enzymes that mediate purine or pyrimidine metabolism and the like.

The nucleic acid sequence of the oligonulcleotide coding for specific genes of interest may be retrieved, without undue experimentation, from the GenBank of EMEL DNA libraries. Such sequences may include coding sequences, for example, the coding sequences for structural proteins, hormones, receptors and the like, and the DNA sequences for other DNAs of interest, for example, transcriptional and translational regulatory elements (promoters, enhancers, terminators, signal sequences and the like), vectors (integrating or autonomous), and the like. Non-limiting examples of DNA sequences which may be introduced into cells include those sequences coding for fibroblast growth factor (see WO 87/01728); ciliary neurotrophic factor (Lin et al., Science, 246:1023, 1989); human interferon-α receptor (Uze, et al., Cell, 60:225, 1990); the interleukins and their receptors (reviewed in Mizal, FASE J., 3:2379, 1989); hybrid interferons (see EPO 051,873); the RNA genome of human rhinovirus (Callahan, Proc. Natl. Acad. Sci., 82:732, 1985); antibodies including chimeric antibodies (see U.S. Pat. No. : 4,816,567); reverse transcriptase (see Moelling, et al., J. Virol., 32:370, 1979); human CD4 and soluble forms thereof (Maddon et al., Cell, 47:333, 1986, WO 88/01304 and WO 89/01940); and EPO 330,191, which discloses a rapid immunoselection cloning method useful for the cloning of a large number of desired proteins.

Aggregates can be used in antisense inhibition of gene expression in a cell by delivering an antisense oligonucleotide into the cell (see Wagner, Science 260:1510, 1993 and WO 93/10820). Such oligonucleotides will generally comprise a base sequence that is complementary to a target RNA sequence that is expressed by the cell. However, the oligonucleotide may regulate intracellular gene expression by binding to an intracellular nucleic acid binding protein (see Clusel, *Nuc. Acids Res.* 21:3405, 1993) or by binding to an intracellular protein or organelle that is not known to bind to nucleic acids (see WO 92/14843). A cell that is blocked for expression of a specific gene(s) is useful for manufacturing and therapeutic applications. Exemplary manufacturing uses include inhibiting protease synthesis in a cell to increase production of a protein for a therapeutic or diagnostic application (e.g., reduce target protein degradation caused by the protease). Exemplary therapeutic applications include inhibiting synthesis of cell surface antigens to reduce rejection and/or to induce immunologic tolerance of the cell either after it is implanted into a subject or when the cell is transfected in vivo (e.g. histocompatibility antigens, such as MHC class II genes, and the like).

Methods to introduce aggregates into cells in vitro and in vivo have been previously described (see U.S. Pat. Nos.: 5,283,185 and 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Entry of liposomes or aggregates into cells may be by endocytosis or by fusion of the liposome or aggregate with the cell membrane. When fusion takes place, the liposomal membrane is integrated into the cell membrane and the aqueous contents of the liposome merge with the fluid in the cell.

Endocytosis of liposomes occurs in a limited class of cells; those that are phagocytic, or able to ingest foreign particles. When phagocytic cells take up liposomes or aggregates, the cells move the spheres into subcellular organelles known as lysosomes, where the liposomal membranes are thought to be degraded. From the lysosome, the liposomal lipid components probably migrate outward to become part of cell's membranes and other liposomal components that resist lysosomal degradation (such as modified oligonucleotides or oligomers) may enter the cytoplasm.

Lipid fusion involves the transfer of individual lipid molecules from the liposome or aggregate into the plasma membrane (and vice versa); the aqueous contents of the liposome may then enter the cell. For lipid exchange to take place, the liposomal lipid must have a particular chemistry in relation to the target cell. Once a liposomal lipid joins the cell membrane it can either remain in the membrane for a period of time or be redistributed to a variety of intracellular membranes. The cationic lipids of the present invention can be used to deliver an expression vector into a cell for manufacturing or therapeutic use. The expression vectors can be used in gene therapy protocols to deliver a therapeutically useful protein to a cell or for delivering nucleic acids encoding molecules that encode therapeutically useful proteins or proteins that can generate an immune response in a host for vaccine or other immunomodulatory purposes according to known methods (see U.S. Pat. Nos.: 5,399,346 and 5,336,615, WO 94/21807 and WO 94/12629). The vector-transformed cell can be used to produce commercially useful cell lines, such as a cell line for producing therapeutic proteins or enzymes (e.g. erythropoietin, and the like), growth factors (e.g. human growth hormone, and the like) or other proteins. The aggregates may be utilized to develop cell lines for gene therapy applications in humans or other species including murine, feline, bovine, equine, ovine or non-human primate species. The aggregates may be used to deliver anionic macromolecules into cells in tissue culture medium in vitro or in an animal in vivo.

To assist in understanding the present invention, the following examples are included which describe the results of a series of experiments. The following examples relating to this invention should not, of course, be construed as specifically limiting the invention. Variations of the invention, now known or later developed, which would be within the purview of one skilled in the art are considered to fall within the scope of the invention as described herein and hereinafter claimed.

EXAMPLES

General Methods

All reactions were run under a positive pressure of dry argon. Reactions requiring anhydrous conditions were performed in flame-dried glassware which was cooled under argon. Tetrahydrofuran (THF, Aldrich Milwaukee, Wis.) was distilled from potassium/benzophenone ketyl immediately prior to use. Methylene chloride, pyridine, toluene, heptane, methanol, and ethanol were obtained as anhydrous reagent (<0.005% water) or reagent grade and were used without further purification. TLC was performed on 0.2 mm E. Merck precoated silica gel 60 $F_{254}$ TLC plates (20×20 cm aluminum sheets, Fisher, Pittsburgh, Pa.). Flash chromatography was performed using E. Merck 230-400 mesh silica gel. All $^1H$, $^{13}C$ and $^{31}P$ NMR spectra were recorded on a 300 MHz Bruker ARX Spectrometer (Bruker, Boston, Mass.) and were obtained in $CDCl_3$ unless otherwise indicated. Mass spectra were provided by The Scripps Research Institute Mass Spectrometry Facility of La Jolla, Calif. FAB mass spectra were obtained on a FISONS VG ZAB-VSE double focusing mass spectrometer equipped with a cesium ion gun (Fisions, Altrincham, UK). ESI mass spectra were obtained on an API III PE Sciex triple-quadrupole mass spectrometer (Sciex, Toronto, Calif.).

Example 1

Synthesis of $N^2,N^5$-Bis[(1,1-Dimethylethoxy)Carbonyl]-$N^2,N^5$-Bis[3-[(1,1-Dimethylethoxy) Carbonyl]Aminopropyl]-L-Ornithine, N-Hydroxysuccinimydyl Ester (1-2)

A 100 ml round-bottomed reaction flask was charged with (2.08 g, 3.2 mmol) of $N^2,N_5$-Bis[(1,1-dimethylethoxy) carbonyl]-$N^2$ $N_5$-bis[3-[(1,1-dimethylethoxy)carbonyl] aminopropyl]-L-ornithine (Behr, J. P. *Acc. Chem. Res.* 26:274, 1993), dicyclohexylcarbodiimide (0.73 g, 3.5 mmol), N-hydroxysuccinimide (0.41 g, 3.5 mmol), and methylene chloride (20 mL). The reaction mixture was stirred for 5 hours and then placed in a refrigerator (0° to 5° C.) overnight (15 hours). This mixture was filtered and washed with methylene chloride, and the filtrate was concentrated by rotary vaporization. The crude product was purified by flash chromatography on silica gel using 1:1 ethyl acetate:heptane to provide 1.2 g (50% yield) of 1-2 as a white solid: $^1H$ NMR-5.26 (br s, 1 H), 4.77 (br s, 1 H), 4.28 (br s, 1 H), 3.22–3.09 (m, 10 H), 2.84 (s, 4 H), 2.05–1.61 (m, 8 H), 1.48 and 1.46 and 1.44 (3 s, 36 H); MS (ESI) m/z 744 ($MH^+$).

Example 2

N',N'-Dioctadecyl—[$N^α$-butyloxycarbonyl-$O^g$-benzyl]-L-glutamine (3-1)

Approximately 3.3 mmol of dioctadecylamine, 3.0 mmol of N-hydroxybenzotriazole, and 3.0 mmol of dicyclohexylcarbodiimide (3 mmol) was added to a solution of N—Boc-$O^Y$-benzyl-L-glutamic acid (3 mmol) in dichloromethane (30 mL). The reaction proceeded at room temperature for 21 hours. The precipitated dicylohexylurea was removed by filtration and the reaction mixture was washed with water, saturated sodium bicarbonate and brine, and dried with magnesium sulfate. The product was purified by column chromatography on silica gel (heptane/ethyl acetate, 3:1)

(see Scheme 3). 2 g, 80% yield. $^1$H NMR (300 MHz, CDCl$_3$, TMS=0) d 7.36–7.50(m, 5H), 5.38 (d, 1H, J=8.6), 5.13 (s, 2H), 4.64 (m, 1H), 3.48 (m, 2H), 3.22–3.05 (m, 2H), 2.47 (m, 2H), 2.05 (m, 1H), 1.75 (m, 1H), 1.65–1.35 (m, 4H), 1.42(s,9H), 1.25(bs, 60H), 0.88 (t, 6H, J=6.8).

Example 3
Synthesis of [N",N",N"-tris-[N'N'-Dioctadecyl-L-glutamide]]tris[2-aminoethyl]amide (3-2)

Approximately 140 mg of Pearlman's catalyst was added to a solution of compound 3-1 (1.2 mmol) in ethyl acetate (50 mL). The reaction mixture was placed under 50 psi of hydrogen for 1.5 hours. The catalyst was removed by filtration through Celite, and the solvent was removed. A solution of the debenzoylated, lipidic amino acid (1.2 mmol) and tris(2-aminoethyl)amine (0.31 mmol) was prepared in dichloromethane (12 mL). N-Hydroxybenzotriazole (1 mmol) and dicyclohexylcarbodiimide (1 mmol) were added in succession, and the reaction proceeded at room temperature for 24 hours. Dichloromethane was added, and the organic solution was washed with saturated sodium bicarbonate and brine, and dried with anhydrous magnesium sulfate. The product was purified by chromatography on silica gel (5% methanol in dichloromethane) producing 326 mg (45% yield). $^1$H NMR (300 MHz, CDCl$_3$, TMS=0) d 6.98 (bs, 3H), 5.67 (bd, 3H) 4.50 (m, 3H), 3.60–3.00 (m, 20H), 2.62 (bs, 6H), 2.29 (m, 6H), 2.00–1.40 (m, 22H), 1.42 (s, 18H), 1.25 (bs,190H), 0.88 (t, 18H, J=6.9).

Example 4
Synthesis of [N",N",N"-tris-[N',N'-Dioctadecyl-L-6-Carboxyspermyl -L-Glutamine]]Tris [2-Aminoethyl]Amide Tridecahydrotrifluoroacetate (3-3)

Boc-protected trimer compound 3-2 was deprotected in trifluoroacetic acid:1,2-dichloroethane (1:1; 5 mL) for 20 minutes. The residue was coevaporated from heptane yielding the desired product. A solution of the deprotected trimer (0.14 mmol) and Hunig's base (1.4 mmol) was prepared in dichloromethane (10 mL). Approximately 0.63 mmol of compound 1-2 in 3.0 ml of dichloromethane. The reaction proceeded at room temperature for 12 hours. Dichloromethane was added to the reaction mixture, and the organic solution was washed with water and brine, and dried with anhydrous magnesium sulfate. The product was purified by column chromatography on silica gel (7% methanol in dichloromethane; R$_f$=0.2). The Boc-protected product (100 mg) was deprotected in trifluoroacetic acid/1,2-dichloroethane (1:1; 5 mL) for 40 minutes at room temperature. After coevaporation from heptane the product was placed on high vacuum overnight yielding a white solid (100 mg). $^1$H NMR (300 MHz, CDCl$_3$+CD$_3$OD, TMS =0) d 4.01 (m, 3H), 3.65—2.95 (m, 54H), 2.33 (m, 6H), 2.25–1.60 (m, 42H), 1.52 (m, 10H), 1.28 (bs, 180H), 0.89 (t, 18H, J=6.6); ESIMS m/z calculated for C$_{162}$H$_{330}$N$_{22}$O$_9$:2730, found 2731 (M+H)$^+$.

Example A
Preparation and transfection protocols for COS-7, SNB-19 RD, and C8161 cells with mixtures of cationic lipids and CAT plasmid
A. Culturing and Transfection of Cells Cell lines were plated at 1.5×10$^5$ cells/well in a 12 well plate format on the day before transfection. Cultures were maintained at 37° C. in 5% CO$_2$. On the next day, when the cells reached approximately 80% confluence, the transfection mixes were prepared as follows: 126 μg of the target CAT plasmid pG1035 (described below) was added to 36.0 mL of Opti-MEM® (Gibco/BRL, Gaithersburg, Md.) to make a plasmid stock solution. 63 μg of each lipid mix (from a high concentration stock in 100% ethanol) was added to individual 1.5 mL aliquots Opti-MEM® and mixed thoroughly. Then, 2 mL of the DNA stock (containing 7 μg of plasmid) were added to each 1.5 mL aliquot of lipid/Opti-MEM® and gently vortexed. This procedure yielded 3.5 mL of plasmid/lipid mixture at 2 μg/mL plasmid and 18 μg/mL lipid for a 9 to 1 lipid to DNA ratio. The quantity of ethanol in the final cell cultures was 2% or less. This small quantity of ethanol was confirmed to have no adverse effect on any of the cell lines.

In order to prepare cells for transfection, the culture medium was aspirated from the wells and the cells were rinsed twice in 1 mL Opti-MEM® per well. The transfection experiments were performed in triplicate; thus, 1 mL of each transfection mix was then added to each of three wells. The cells were cultured in the transfection mix for 5 to 6 hours. The transfection mix was then removed and replaced with 1 mL of complete culture medium (DMEM or DMEM/F12 plus 10% fetal bovine serum and 1/100 dilution of penicillin/streptomycin stock, all from Gibco/BRL, (Gaithersburg, Md.) and the cells were allowed to recover overnight before expression of the CAT gene was measured.

Cell lysates were prepared by rinsing twice in PBS and then were treated with 0.5 mL of 1X Reporter Lysis Buffer (Promega, Madison, Wis.). The lysed cells were pipetted into 1.5 mL tubes and frozen in CO$_2$/EtOH once and thawed. The crude lysate was then clarified by microcentrifugation at 14,000 rpm for 10 minutes to pellet cell debris. The clear supernatant was recovered and assayed directly or stored at −20° C. for assay later.

The cell lysates were then assayed for CAT activity and the total protein concentration was determined as described herein. The CAT activity was normalized to total protein and plotted as shown.

B. Chloramphenicol Acetyltransferase Assay

This assay was performed generally as follows. First, the following reaction mixture was prepared for each sample:

65 mL 0.23 M Tris, pH 8/0.5% BSA (Sigma, St. Louis, Mo.), 4 mL $^{14}$C-chloramphenicol, 50 nCi/mL (Dupont, Boston, Mass.), and 5 mL mg/mL n-butyryl coenzyme A (Pharmacia, Piscataway, N.J.).

A CAT activity standard curve was prepared by serially diluting CAT stock (Promega, Madison, Wis.) 1:1000, 1:10, 000 and 1:90,000 in 0.25M Tris, pH 8/0.5% BSA. The original stock CAT was at 7000 Units/mL. CAT lysate was then added in a labeled tube with Tris/BSA buffer to a final volume of 50 mL.

Approximately 74 mL of reaction mixture was then added to each sample tube, which was then typically incubated for approximately 1 hour in a 37° C. oven. The reaction was terminated by adding 500 mL pristane:mixed xylenes (2:1) (Sigma, St. Louis, Mo.) to each tube. The tubes were then vortexed for 2 minutes and spun for 5 minutes. Approximately 400 mL of the upper phase was transferred to a scintillation vial with 5 mL Scintiverse (Fisher, Pittsburgh, Pa.). The sample was then counted in a scintillation counter (Packard).

C. Coomassie Protein Assay

The total protein content of the clarified cell lysates was determined by mixing 6 mL of each cell lysate to 300 mL of Coomassie protein assay reagent (Pierce, Rockford, Md.) in the wells of an untreated microtiter assay plate. Concentration curve standards were prepared using 6 mL of 0, 75, 100, 200, 250, 400, 500, 1000, and 1500 mg/mL BSA stock solutions and 300 mL of the Coomassie reagent. The assay samples were allowed to sit for approximately 30 minutes before reading the optical absorbance at 570 nm in a microplate reader (Molecular Probes).

The cells were assayed for CAT protein as described above. The results of the transfection efficiency of a mixture of 3-3 and Lipid P is tabulated in Table 1.

Example B

FITC-Oligonucleotide Uptake Assay

A. Oligomers Used

The oligonucleotides used for the determination of cationic lipid mediated oligonucleotide uptake in all cell lines tested are:

3498-PS: 5' FITC-ggt-ata-tcc-agt-gat-ctt-ctt-ctc [SEQ. ID NO. 1],

Oligomer 3498-PS has an all-phosphorothioate backbone. This oligonucleotide has 23 negative charges on the backbone and is considered to be 100% negatively charged.

3498: 5' FITC-ggt-ata-tcc-agt-gat-ctt-ctt-ctc [SEQ. ID NO. 2],

Oligomer 3498 is a chimeric oligonucleoside. The underlined bases were linked by a phosphorothioate backbone, while the other linkages in the oligomer consisted of alternating methylphosphonates and phosphodiesters. The oligomer had 11 methylphonate, 7 diester, and 5 phosphorothioates linkages. The total charge density was 57% of 3498-PS.

3793-2: 5' FITC-ggu-aua-ucc-agu-gau-cuu-cut [SEQ. ID NO. 3],

Oligomer 3293-2 has an alternating methylphosphonate and diester backbone with all 2'-O-methyl groups on each ribose in the oligonucleotide. The total charge density was 50% of 3498-PS.

Stocks of oligomers 3498-PS and 3498 are prepared at 300 micromolar, while the oligomer 3793-2 stock is prepared at 440 micromolar.

B. Reagents and Cells

The commercially available lipids used in the assays were: Lipofectin® ("LFN") Lot#EF3101 1 mg/mL, Gibco/BRL (Gaithersburg, Md.) LipofectAMINE® ("LFA") Lot#EFN101 2 mg/mL, Gibco/BRL (Gaithersburg, Md.) Transfectam® ("TFM") Lot#437121 1 mg dry, Promega, (Madison, Wis.) and resuspended in 100% ethanol.

The novel lipids of the present invention used in these evaluations, are at 1 mg/mL in 100% ethanol.

The tissue culture cell stocks, SNB-19 (human glioblastoma), C8161 (a human amelanotic melanoma), RD (human rhabdomyosarcoma, ATCC # CCL-136) and COS-7 (African green monkey kidney cells, ATCC # CRL-1651) are maintained in standard cell culture media: DMEM:F12 (1:1) mix from Mediatech, Lot#150901126, 10% fetal bovine serum from Gemini Bioproducts, Lot#A1089K, 100 units/mL penicillin and 100 micrograms/mL streptomycin, from Mediatech, Lot#30001044 and 365 micrograms/mL L-glutamine. The cells are maintained under standard conditions (37° C., 5% $CO_2$ atmosphere) at all times prior to fixation and microscopic examination.

C. Preparation of Cells and Transfection Mixes

For each FITC labeled oligomer delivery determination, the appropriate cells are plated into 16 well slides (Nunc #178599, glass microscope slide with 16 removable plastic wells attached to the slide surface with a silicone gasket) according to standard tissue culture methods. Each cell line is plated at a starting density (approximately 20,000 cells/well) that allowed them to be healthy and 60–80% confluent one to two days after plating. The cells are allowed to adhere to the glass and recover from the plating procedure in normal growth medium for 24 to 48 hours before beginning the transfection procedure.

Oligonucleotide transfection mixes are made up in Opti-MEM® without antibiotics as follows: 500 mL aliquots of Opti-MEM® containing a 0.25 micromolar solution of either oligomer 3498-PS, 3498, or 3793-2 (2 micrograms of oligomer per sample) are pipetted into 1.5 mL Eppendorf tubes. Cationic lipid or lipid mixture is then added to the oligomer solution to give a final 9:1 or 6:1 ratio (18 or 12 mg of lipid total) of cationic lipid to oligomer by weight. The tubes are mixed by vortexing immediately after the addition of lipid.

Prior to beginning the transfection reactions the cells are rinsed in 200 μL Opti-MEM®; then, the cells are rinsed with Dulbecco's phosphate buffered saline (PBS) solution, and 200 μL of oligomer transfection mix is added directly to a well to begin each transfection reaction. Transfection reactions are allowed to continue for four to six hours.

At that time, the cells are then rinsed in PBS from Mediatech and fixed for ten minutes in 200 μL of 3.7% formaldehyde (Sigma, St. Louis, Mo.) to terminate the transfection reaction. Then the wells are rinsed again in PBS. The formaldehyde is quenched with 200 μL of 50 mM glycine (Sigma, St. Louis, Mo.) for ten minutes. Finally, the wells are then emptied by shaking out the glycine solution. At that time, the plastic chambers and silicone gasket are removed and the cells are covered with Fluoromount-G mounting medium (from Fisher, Pittsburgh, Pa., with photobleaching inhibitors) and a cover slip.

Intracellular fluorescence is evaluated under 200X magnification with a Nikon Labophot-2 microscope with an episcopic-fluorescence attachment. Using this equipment we can distinguish extracellular from nuclear and endosomal fluorescence.

The cells are scored for uptake of FITC labelled oligomer as follows: No nuclear fluorescence, 0; up to 20% fluorescent nuclei, 1; up to 40% fluorescent nuclei, 2; up to 60% fluorescent nuclei, 3; up to 80% fluorescent nuclei, 4; and up to 100% fluorescent nuclei, 5.

TABLE 1

Demonstration of plasmid delivery and expression in SNB-19 with a lipid 3-3/Lipid P mixture

| Cell line | Lipid | CAT cpm/ug ave. | SDV |
|---|---|---|---|
| SNB-19 | Lipofectin | 742 | 72 |
|  | 3-3/Lipid P | 4321 | 601 |

We claim:

1. A compound of the formula

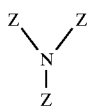

wherein Z is

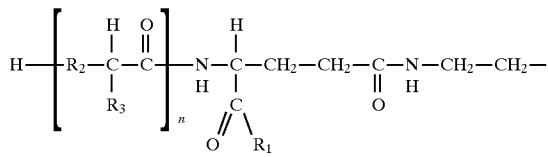

wherein
(a) n is 0, 1 or 2;
(b) $R_1$ is hydroxy, a glyceryl moiety or a lipophilic moiety;
(c) $R_2$ is
  (i) —NH-[alk$_1$—NH]$_{n1}$—
    wherein n1 is an integer from 0 to 2 and alk$_1$ is an alkylene group of 2 to 6 carbon atoms;
  (ii) -[W$_1$]$_{n2}$-
    wherein n2 is an integer from 0 to 3 and each W$_1$ is an independently selected amino acid residue;
  (iii) —N(R$_4$) (alk$_2$-) wherein R$_4$ is hydrogen, alkyl of 1 to 18 carbon atoms optionally mono-, di-or tri-substituted with Y$_1$, Y$_2$ and/or Y$_3$; alkenyl of 2 to about 12 carbon atoms, aryl of about 6 to 14 carbon atoms and aralkyl of about 7 to about 15 carbon atoms and alk$_2$ is a straight chained or branched chain alkylene group of 1 to 18 carbon atoms optionally mono-, di-or tri-substituted with Y$_1$, Y$_2$ and/or Y$_3$; where Y$_1$, Y$_2$ and Y$_3$ are independently selected from the group consisting of arylamine of 5 to about 10 carbon atoms, aralkylamine of 5 to about 10 carbon atoms, heterocylic amine, fluorine, a guanidinium moiety, an amidinium moiety, —NH$_2$, —NHR$_{10}$, —NR$_{10}$R$_{11}$ and —N (R$_{10}$R$_{11}$R$_{12}$) wherein R$_{10}$, R$_{11}$ and R$_{12}$ are as defined hereinbelow;
(d) $R_3$ is
  (i) —NH-[alk$_3$]$_{n3}$—H wherein n3 is an integer from 0 to 4 and alk$_3$ is an alkylene group of 2 to 6 carbon atoms;
  (ii) -[W$_2$]$_{n4}$H wherein n4 is an integer from 0 to 3 and each W$_2$ is an independently selected amino acid residue;
  (iii) a negatively charged group selected from the group consisting of -alk$_4$C (O)O$^-$; -alk$_4$—S (O$_2$)O$^-$; -alk$_4$P (O) (O$^-$)O$^-$ and -alk$_4$OP (O) (O$^-$) (O$^-$) wherein alk$_4$ is an alkylene group of 1 to 6 carbon atoms;
  (iv) heterocyclo of 4 to about 10 ring atoms with the ring atoms selected from carbon and heteroatoms, wherein the heteroatoms are selected from the group consisting of oxygen, nitrogen and S(O)$_i$ wherein i is 0, 1 or 2;
  (v) alkyl of 1 to about 12 carbon atoms optionally substituted with a substituent selected from fluoro, a guanidinium moiety, an amidinium moiety, —NH$_2$, —NHR$_{10}$, —NR$_{10}$R$_{11}$ or NR$_{10}$R$_{11}$R$_{12}$ wherein each of R$_{10}$, R$_{11}$ and R$_{12}$ is independently selected from alkyl of 1 to about 12 carbon atoms, alkyl of 1 to about 12 carbon atoms substituted with 1 to about 25 fluorine atoms and alkenyl of 2 to about 12 carbon atoms; or
  (vi) W$_3$—(CH$_2$)$_t$—NH—(CH$_2$)$_q$-wherein t and q are independently selected integers from 2 to 6 and W$_3$ is a guanidinium moiety, an amidinium moiety, —NH$_2$, —NHR$_{10}$, —NR$_{10}$R$_{11}$ or —NR$_{10}$R$_{11}$R$_{12}$ wherein R$_{10}$, R$_{11}$ and R$_{12}$ are as defined herein above, and pharmaceutically acceptable salts thereof.

2. The lipid according to claim 1 wherein R$_1$ is an alkyl or alkenyl moiety of about 10 to about 50 carbon atoms.

3. The lipid according to claim 2 wherein R$_1$ is —C$_{18}$H$_{37}$.

4. The lipid according to claim 1 wherein R$_1$ is a steroidyl moiety.

5. The lipid according to claim 4 wherein the steroidyl moiety is cholesteryl.

6. The lipid according to claim 1 wherein R$_1$ is —OCH (R$_6$R$_7$), wherein R$_6$ and R$_7$ are alkyl moieties of about 10 to about 50 carbon atoms.

7. The lipid according to claim 1 wherein R$_1$ is —NH (R$_8$) or —N (R$_8$R$_9$), wherein R$_8$ and R$_9$ are independently an alkyl or alkenyl moiety of about 10 to about 50 carbon atoms.

8. The lipid according to claim 7 wherein R$_1$ is —N(R$_8$R$_9$), where R$_8$, and R$_9$ are each —C$_{18}$H$_{37}$.

9. The lipid according to claim 1 wherein R$_1$ is a cyclic amine moiety of about 4 to about 10 carbon atoms.

10. The lipid according to claim 1 wherein R$_2$ is —N (R$_4$) (alk$_2$)-.

11. The lipid according to claim 1 wherein R$_2$ is -[W$_1$] n$_2$.

12. The lipid according to claim 11 wherein W$_1$ is a substituted amino acid residue is optionally substituted with an alkyl of 1 to about 12 carbon atoms or wherein the amino group(s) is substituted to form a secondary, tertiary, or quaternary amine with an alkyl moiety of 1 to about 12.

13. The lipid according to claim 11 wherein W$_1$ is an amino acid residue is selected from the group consisting of lysine, arginine, histidine, ornithine, tryptophan, phenylalanine, and tyrosine.

14. The lipid according to claim 11 wherein W$_1$ is an amino acid analog is selected from the group consisting of 3-carboxyspermidine, 5-carboxyspermidine, 6-carboxyspermine and monoalkyl, dialkyl, or peralkyl substituted derivatives which are substituted on one or more amine nitrogens with a alkyl group of 1 to about 12 carbon atoms.

15. The lipid according to claim 1 wherein R$_2$ is —NH-[alk$_1$—NH]$_{n1}$.

16. The lipid according to claim 15 wherein alk$_1$ is —(CH$_2$)$_3$-.

17. The lipid according to claim 16 wherein n$_1$ is 2.

18. The lipid according to claim 16 wherein n$_1$ is 1.

19. The lipid according to claim 15 wherein R$_3$ is W$_3$—(CH$_2$)$_t$—NH—(CH$_2$)$_q$.

20. The lipid according to claim 19 wherein W$_3$ is —NH$_2$.

21. The lipid according to claim 20 wherein t and q are each 3.

22. The lipid according to claim 1 wherein R$_3$ is —NH-[alk$_3$]$_{n3}$—H, -[W$_2$]$_{n4}$H, or W$_3$—(CH$_2$)$_t$—NH—(CH$_2$)$_q$—.

23. The lipid according to claim 1 wherein R$_3$ is a negatively charged group.

24. The lipid according to claim 1 wherein R$_3$ is alkyl of 1 to about 12 carbon atoms optionally substituted with a substituent selected from —F, a guanidinium moiety, an amidinium moiety, —NH$_2$, —NHR$_{10}$, —N(R$_{10}$R$_{11}$), and —N (R$_{10}$R$_{11}$R$_{12}$) wherein R$_{10}$, R$_{11}$, and R$_{12}$.

25. The lipid according to claim 1 wherein R$_3$ is W—(CH$_2$)$_t$—NH—(CH$_2$)$_q$ W$_3$—(CH$_2$)$_t$—NH—(CH$_2$)$_q$ wherein W$_3$ is NH$_2$.

26. The lipid according to claim 25 wherein p and q are 3.

27. The lipid according to claim 1 further comprising [X$^-$]$_m$ wherein X$^-$ is a pharmaceutically acceptable anion or polyanion and m is an integer selected such that [X$^{-1}$]$_m$ is equal to a positive charge of the lipid.

28. The lipid according to claim 1 having the structure:

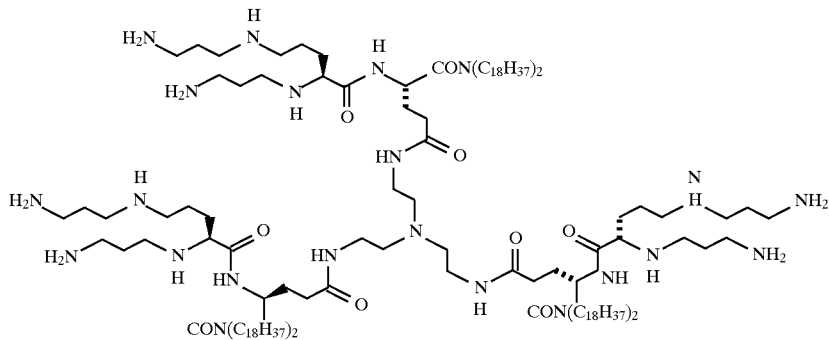

29. A composition comprising a anionic macromolecule and a lipid according to claim 1.

30. The composition according to claim 29 wherein the anionic macromolecule comprises an expression vector capable of expressing a polypeptide in a cell.

31. The composition according to claim 29 wherein the anionic macromolecule is an oligonucleotide or an oligomer.

32. The composition according to claim 29 wherein the anionic macromolecule is DNA or RNA.

33. A method of delivering an anionic macromolecule into a cell comprising contacting the composition of claim 29 with the cell.

34. A method to interfere with the expression of a protein in a cell comprising contacting the composition of claim 31 with the cell wherein the oligomer has a base sequence that is substantially complimentary to an RNA sequence in the cell that encodes the protein.

35. A composition which comprises the lipid of claim 1 and Lipid P.

36. A composition which comprises the lipid of claim 19 and Lipid P.

37. A composition which comprises the lipid of claim 27 and Lipid P.

* * * * *